US011064980B2

(12) United States Patent
Papenfuss et al.

(10) Patent No.: US 11,064,980 B2
(45) Date of Patent: Jul. 20, 2021

(54) FLEXIBLE TISSUE COLLECTION DEVICE

(71) Applicant: Lenkbar, LLC, Naples, FL (US)

(72) Inventors: Erik H. Papenfuss, Naples, FL (US);
Timothy M. O'Brien, Naples, FL (US);
Robert E. Marx, Naples, FL (US)

(73) Assignee: Lenkbar, LLC, Naples, FL (US)

( * ) Notice: Subject to any disclaimer, the term of this patent is extended or adjusted under 35 U.S.C. 154(b) by 773 days.

(21) Appl. No.: 15/240,080

(22) Filed: Aug. 18, 2016

(65) Prior Publication Data
US 2018/0049727 A1 Feb. 22, 2018

(51) Int. Cl.
*A61B 10/02* (2006.01)
*A61B 17/16* (2006.01)

(52) U.S. Cl.
CPC ........ *A61B 10/025* (2013.01); *A61B 10/0283* (2013.01); *A61B 17/1635* (2013.01); *A61B 2010/0258* (2013.01)

(58) Field of Classification Search
CPC .................................................... A61B 10/25
See application file for complete search history.

(56) References Cited

U.S. PATENT DOCUMENTS

| | | | |
|---|---|---|---|
| 6,238,400 B1 * | 5/2001 | Bays | A61B 17/1688 606/96 |
| 7,462,181 B2 | 12/2008 | Kraft | |
| 8,002,733 B2 | 8/2011 | Kraft | |
| 8,043,253 B2 | 10/2011 | Kraft | |
| 8,109,919 B2 | 2/2012 | Kraft | |
| 8,366,559 B2 | 2/2013 | Papenfuss | |

(Continued)

FOREIGN PATENT DOCUMENTS

| | | |
|---|---|---|
| WO | 03101308 A1 | 12/2003 |
| WO | 2012047984 A1 | 4/2012 |
| WO | 2015109100 A1 | 7/2015 |

OTHER PUBLICATIONS

Kraft, D., et al., "Development of the "MarrowMiner": A novel, minimally invasive device for the harvest of bone marrow. From benchtop, to animal studies, through FDA approval and human evaluation", Feb. 2010, p. S167, vol. 16(2), Supplement 2, Biology of Blood and Marrow Transplantation, 2 pages.

(Continued)

*Primary Examiner* — Daniel L Cerioni
*Assistant Examiner* — Yasmeen S Warsi
(74) *Attorney, Agent, or Firm* — RatnerPrestia

(57) ABSTRACT

An instrument for collecting tissue from a body cavity includes a hollow tubular body having a tubular wall. The hollow tubular body can collect material from a body cavity in a coring mode or an aspiration mode. The tubular wall defines a passage that extends from a proximal end portion of the tubular body to a distal end portion of the tubular body. A middle section of the tubular body includes an articulating section that allows the middle section to articulate relative to the proximal end portion. The distal end portion includes at least one suction port extending from an outer wall surface to an inner wall surface of the tubular wall. The suction port provides a path of fluid communication between the outer wall surface and the passage for drawing in tissue from a body cavity when the tubular body is connected to a source of negative pressure.

25 Claims, 11 Drawing Sheets

(56) References Cited

U.S. PATENT DOCUMENTS

| | | |
|---|---|---|
| 8,852,119 B2 | 10/2014 | Wawrzyniak |
| 9,131,925 B2 | 9/2015 | Kraft |
| 2008/0177200 A1* | 7/2008 | Ikehara ................ A61B 10/025 600/567 |
| 2009/0105775 A1 | 4/2009 | Mitchell et al. |
| 2016/0000991 A1 | 1/2016 | Kraft |

OTHER PUBLICATIONS

International Search Report and Written Opinion for International Application No. PCT/US2017/047265, dated Jan. 22, 2018, 17 pages.
Invitation to Pay Additional Fees and Partial International Search Report dated Nov. 20, 2017, 12 pages.
International Preliminary Report on Patentability and Written Opinion for International Application No. PCT/US2017/047265, dated Feb. 19, 2019, 10 pages.
European Communication Pursuant to Article 94(3) for European Application No. 17 764 691.6, dated Aug. 3, 2020, 5 pages.

* cited by examiner

FLEXIBLE TISSUE COLLECTION DEVICE

FIELD

The present invention relates generally to instrumentation for collecting tissue from a body cavity, and more particularly to a tissue collection device having a flexible portion.

BACKGROUND

Bone marrow, which is produced and stored inside bone, can be harvested and used for different purposes, including the treatment of congenital defects and diseases, and reconstruction of bone. Bone marrow contains useful components, including hematopoietic stem cells and blood cells. Conventional methods for harvesting bone marrow have historically relied on the use of needles. A needle is advanced through the patient's skin and the wall of a bone until the needle tip enters into the bone cavity containing the marrow. Typically, the needle is advanced into the donor's pelvis, but the needle can also be inserted into other bones. Once the needle penetrates into the bone cavity, the needle advances in a linear path, and the marrow is harvested by aspiration.

Bone marrow harvesting by aspiration often yields a relatively small amount of stem cells because the concentration of stem cells at specific locations is low. To harvest a sufficient amount of marrow and stem cells, the physician must draw a significant volume of marrow which is greater than can be drawn from a single aspiration at one location. Therefore, to collect a sufficient volume of marrow and stem cells, the needle must be inserted into the bone at multiple locations within the bone cavity to draw bone marrow from different areas. This requires multiple punctures through the outer cortex and into the bone cavity to collect the required volume of marrow. Multiple punctures can be time consuming and labor intensive for physicians performing the harvesting. In addition, multiple punctures cause a great deal of pain to the donor and require a long recovery time after the patient is taken off of general anesthesia.

U.S. Pat. No. 7,462,181 to Daniel Kraft and James Hole (hereinafter, "the '181 patent") describes an alternative device for aspirating bone marrow or tissue from a bone cavity. Rather than using a rigid needle that proceeds linearly through bone, the device includes a thin hollow needle that is flexible enough to move through the bone marrow cavity in a non-linear fashion. By advancing the needle in a non-linear path, the needle can access different locations in the bone from a single entry point.

Although the flexible needle in the '181 patent can, in theory, allow more marrow to be collected from a single entry point, collection is only done by aspiration. The flexible needle does not allow bone marrow or tissue to be collected by "coring", in which a core of marrow is removed from the bone cavity in an undisturbed state. Aspiration tends to mix stem cells with blood and other components as the material is collected under suction. This mixing can dilute the concentration of stem cells at a collection point.

Flexible needles are also prone to breakage during procedures due to their very small diameter. This propensity for breakage often requires the use of accessories to reinforce the needle during a harvesting procedure. For example, the '181 patent describes embodiments that utilize a stylet inside the flexible needle when the needle is advanced into the bone marrow. Stylets provide aspiration needles with additional strength and rigidity during advancement through the marrow space. The need for stylets and other accessories increases the number of items that must be sterilized and handled with aspiration needles during a harvesting procedure.

Moreover, flexible hollow needles offer few options for controlling the amount of bending or pivot motion along the length of the needle. Flexible needles with uniform cross sections are generally flexible along their entire length. This may not be desirable in applications where only a section of the shaft needs to bend, while the remainder of the shaft should remain rigid. Flexible needles also lack features to assist in cutting through dense cortical bone or shaving bone.

U.S. Pat. No. 8,852,119 to Kortney Wawrziniak, et al. (hereinafter, "the '119 patent") describes another device for harvesting bone marrow from a bone cavity. The device includes a flexible needle and a trocar with a cannulated shaft. The cannulated shaft of the trocar can be driven into bone to provide an access path into the bone. The cannulated shaft is also configured to receive the flexible needle after being driven into the bone. Once the needle is advanced into a target bone, a receptacle is coupled to the needle to aspirate bone marrow through the needle. The needle can have both a rigid section and a flexible portion extending distally from the rigid section. The flexible portion of the needle is defined by a continuous groove that extends along a helical path.

The needle described in the '119 patent provides some benefits over other needles that are flexible along their entire length. Nevertheless, the needle of the '119 patent only collects bone marrow by aspiration, and does not allow bone marrow or tissue to be collected by coring. In fact, the passage inside the needle terminates short of the distal end, where the passage aligns with intake ports on the side of the needle. Moreover, the intake ports on the side of the needle are recessed to prevent material other than aspirate from entering the needle. In this arrangement, the needle passage cannot receive a core of material because the passage is essentially closed off. Therefore, the needle is limited in how it can harvest marrow and collect material inside bone.

For all of the foregoing reasons, conventional devices and techniques for harvesting bone marrow have significant shortcomings.

SUMMARY

The shortcomings of conventional devices and techniques for harvesting bone marrow are resolved by instruments and methods in accordance with the present invention, examples of which are described herein.

In one beneficial aspect of the invention, an instrument for collecting tissue from a body cavity can include a hollow tubular body. The tubular body can include a proximal end portion that terminates at a proximal end, a distal end portion that terminates at a distal end, and a middle section extending between the proximal end portion and the distal end portion. The middle section can include a first end contiguous with and next to the proximal end portion, and a second end contiguous with and next to the distal end portion. The tubular body can also include a tubular wall extending between the proximal end and the distal end. The tubular wall can define an outer wall surface and an inner wall surface, and can surround a passage that extends from the proximal end portion of the tubular body to the distal end portion of the tubular body. The tubular body can also include an articulating section that allows a portion of the tubular body to articulate relative to the proximal end portion. The distal end portion can include at least one suction port extending from the outer wall surface to the inner wall surface. The at least one suction port can provide a path of fluid communication between the outer wall surface and the passage for drawing in tissue from a body cavity when the tubular body is connected to a source of negative pressure, and when the distal end portion is placed in proximity to the tissue.

In another beneficial aspect, an instrument for collecting tissue from a body cavity can include a passage that terminates at a proximal end of a tubular body to define a proximal opening in the tubular body, and terminates at a distal end of the tubular body to define a distal opening in the tubular body.

In another beneficial aspect, an instrument for collecting tissue from a body cavity can include a distal end portion that features a plurality of flutes, each flute terminating with a cutting blade at the distal end of the tubular body.

In another beneficial aspect, an instrument for collecting tissue from a body cavity can include at least one flute that includes at least one suction port.

In another beneficial aspect, an instrument for collecting tissue from a body cavity can include at least one suction port that defines an elongated slot that passes through a tubular wall and extends parallel to a longitudinal axis of the instrument.

In another beneficial aspect, an instrument for collecting tissue from a body cavity can include an articulating section that features a plurality of interlocking sections.

In another beneficial aspect, an instrument for collecting tissue from a body cavity can include an articulating section that features a first interlocking section and a second interlocking section.

In another beneficial aspect, an instrument for collecting tissue from a body cavity can include a first interlocking section and a second interlocking section having at least one pin and at least one socket.

In another beneficial aspect, an instrument for collecting tissue from a body cavity can include at least one pin that is substantially triangular shaped, and at least one socket that is substantially triangular shaped.

In another beneficial aspect, an instrument for collecting tissue from a body cavity can include at least one pin on a first interlocking section that has a circumferential width that increases as the at least one pin extends from an outer surface of the shaft to the inner surface of the shaft, so that the at least one pin becomes gradually wider toward the inner surface.

In another beneficial aspect, an instrument for collecting tissue from a body cavity can include at least one pin on a second interlocking section that has a circumferential width that decreases as the at least one pin on the second interlocking section extends from an outer surface of the shaft to an inner surface of the shaft, so that the at least one pin becomes gradually narrower toward the inner surface.

In another beneficial aspect, an instrument for collecting tissue from a body cavity can include first and second interlocking sections that are cut at opposing angles to create at least one inward angled surface and at least one outward angled surface, the at least one inward angled surface being adjacent to the at least one outward angled surface.

In another beneficial aspect, an instrument for collecting tissue from a body cavity can include a tubular body that has a uniform outer diameter along an entire length of the tubular body such that the outer diameters of a proximal end portion, a middle section and a distal end portion are equal.

In another beneficial aspect, an assembly for collecting tissue from a body cavity can include a piercing instrument having a proximal end, a distal end, and a shaft extending between the proximal end and the distal end. The assembly can also include a collection instrument having a hollow tubular body. The tubular body can include a proximal end portion that terminates at a proximal end, a distal end portion that terminates at a distal end, and a middle section extending between the proximal end portion and the distal end portion. The middle section can include a first end contiguous with and next to the proximal end portion, and a second end contiguous with and next to the distal end portion. The tubular body can include a tubular wall extending between the proximal end and the distal end. The tubular wall can define an outer wall surface and an inner wall surface, and can surround a passage that extends from the proximal end portion of the tubular body to the distal end portion of the tubular body. The passage can be adapted to receive at least one portion of the piercing instrument in a telescoping arrangement. The middle section of the tubular body can include an articulating section that allows a portion of the tubular body to articulate relative to the proximal end portion. The distal end portion can include at least one suction port extending from the outer wall surface to the inner wall surface. The at least one suction port can provide a path of fluid communication between the outer wall surface and the passage for drawing in tissue from a body cavity when the tubular body is connected to a source of negative pressure, and when the distal end portion is placed in proximity to the tissue.

In another beneficial aspect, an assembly for collecting tissue from a body cavity can include a piercing instrument having a first handle. The assembly can also include a collection instrument with a second handle that is nestable with the first handle when at least one portion of the piercing instrument is received in a passage of the collection instrument.

In another beneficial aspect, an assembly for collecting tissue from a body cavity includes a source of negative pressure comprising a suction element, and a collection instrument. The collection instrument can include a hub portion and a hollow tubular body, the hub portion having a connecting element for connection to the suction element. The tubular body can include a proximal end portion, a distal end portion, and a middle section extending between the proximal end portion and the distal end portion. The proximal end portion can terminate at a proximal end, and the distal end portion can terminate at a distal end. The middle section can include a first end contiguous with and next to the proximal end portion, and a second end contiguous with and next to the distal end portion. The tubular body can include a tubular wall extending between the proximal end and the distal end. The tubular wall can define an outer wall surface and an inner wall surface, and can surround a passage that extends from the proximal end portion of the tubular body to the distal end portion of the tubular body. The middle section of the tubular body can include an articulating section that allows a portion of the tubular body to articulate relative to the proximal end portion. The distal end portion can include at least one suction port extending from the outer wall surface to the inner wall surface. The at least one suction port can provide a path of fluid communication between the outer wall surface and the passage. The connecting element can be adapted to form a fluid connection between the suction element and the passage for drawing tissue from a body cavity through the suction port and into the passage upon activation of the source of negative pressure when the suction element is connected to the hub portion, and when the distal end portion is placed in proximity to the tissue.

In another beneficial aspect, an assembly for collecting tissue from a body cavity can include a source of negative pressure that either is in the form of, or includes, a syringe.

In another beneficial aspect, an assembly for collecting tissue from a body cavity can include an articulating section featuring a first interlocking section and a second interlocking section.

In another beneficial aspect, an assembly for collecting tissue from a body cavity can include a collection instrument with an articulating section and an outer sleeve positioned over the articulating section to seal the articulating section.

In another beneficial aspect, an assembly for collecting tissue from a body cavity can include a collection instrument with a tubular body, and a source of negative pressure featuring a suction tube that extends into a passage of the tubular body. The suction tube can include a distal end that terminates adjacent to the suction port of the tubular body.

BRIEF DESCRIPTION OF THE DRAWINGS

The summary and detailed description sections will be better appreciated when reviewed in conjunction with the drawing figures. The following drawing figures illustrate exemplary and non-limiting embodiments of the invention, and depict elements which can be combined and arranged either as shown, or in other combinations and arrangements that are contemplated by persons of skill in the art.

DETAILED DESCRIPTION

Figure 1:
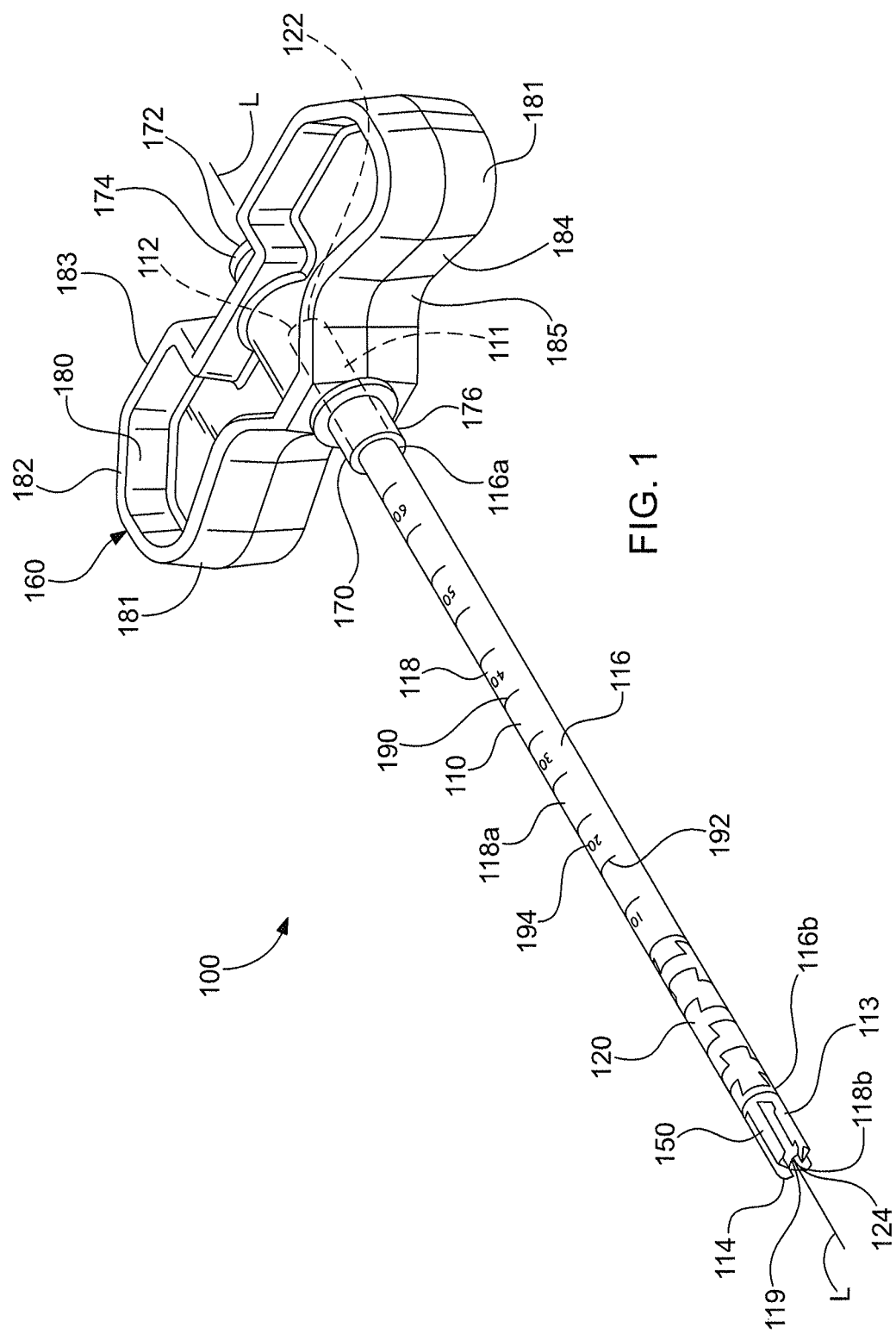
FIG. 1 is a perspective view of a first device in accordance with an embodiment of the invention that can be used for accessing a body cavity and collecting tissue from the body cavity.

The applicant has developed a collection device, assembly and procedure for more efficiently collecting tissue from bodily cavities. The collection device can be utilized for collecting various types of matter from cavities within the body. For purposes of this description, the collection device will be described as it would be used for collecting bone marrow from bone. When used for collecting bone marrow, the bone marrow can be collected for biopsy purposes, for use as a medium for bony regeneration, or for harvesting stem cells to be processed and used for the subsequent treatment of congenital defects, diseases or other conditions.

The collection device features a flexible cannulated shaft that allows for safe and efficient collection of bone marrow from a single entry point into the bone. The preferred flexible shaft is comprised of rigid components, including rigid interlocking segments that collectively form a flexible section. The rigid segments allow the shaft to be advanced though bone marrow without the need for a stylet or other type of structural reinforcement in or around the shaft. The flexible section allows the shaft to yield and bend as it advances through marrow, so as to follow a path of least resistance. Thus, after penetrating through the outer cortex, the flexible shaft can bend and advance along the inner aspect of the bone where higher concentrations of stem cells are found.

The flexibility of the shaft can also prevent the leading end of the shaft from penetrating through a bone wall opposite an entry point, because the flexible section causes the leading end to bend in response to contact with the bone wall. This provides a safe alternative to rigid needles, particularly when used in long bones or other areas in which the cavities are relatively narrow or confined.

Moreover, the flexible shaft can include a distal shaving tip with bone shaving features not present on conventional needles. The shaving features aid in cutting and displacing bone from the outer cortex during initial penetration into the bone. The shaving features can also allow the flexible shaft to cleanly remove a core of bone marrow material when advanced into an area containing a high concentration of stem cells. The core of material is cut cleanly from the surrounding material as the distal shaving tip moves through the material, yielding a core with a high concentration of stem cells preserved inside. By allowing a core of bone marrow to be removed, the stem cells are not diluted or mixed with blood and other matter. This avoids the need to employ subsequent processing such as centrifugation in order to separate the stem cells from other material.

Although the flexible shaft provides the benefit of removing a core of bone marrow, the flexible shaft also allows removal of stem cells by aspiration. This versatility allows the flexible shaft to be a dual purpose or "2-in-1" device that can alternate between being a coring device and an aspiration device, depending on conditions where the marrow is being collected. For example, the flexible shaft can be advanced through a non-linear trajectory in bone to cleanly remove a core of bone marrow from the bone. Once the core of bone marrow is retrieved from the flexible shaft, the flexible shaft can be reinserted into the bone through the same entry point, and advanced through the same trajectory to the location previously occupied by the core. The area previously occupied by the core is typically replaced by fluids containing stem cells, blood and other components. At this stage, the flexible shaft can be attached to a source of negative pressure, such as a syringe, to remove the stem cell-containing fluid by aspiration.

Figure 2:
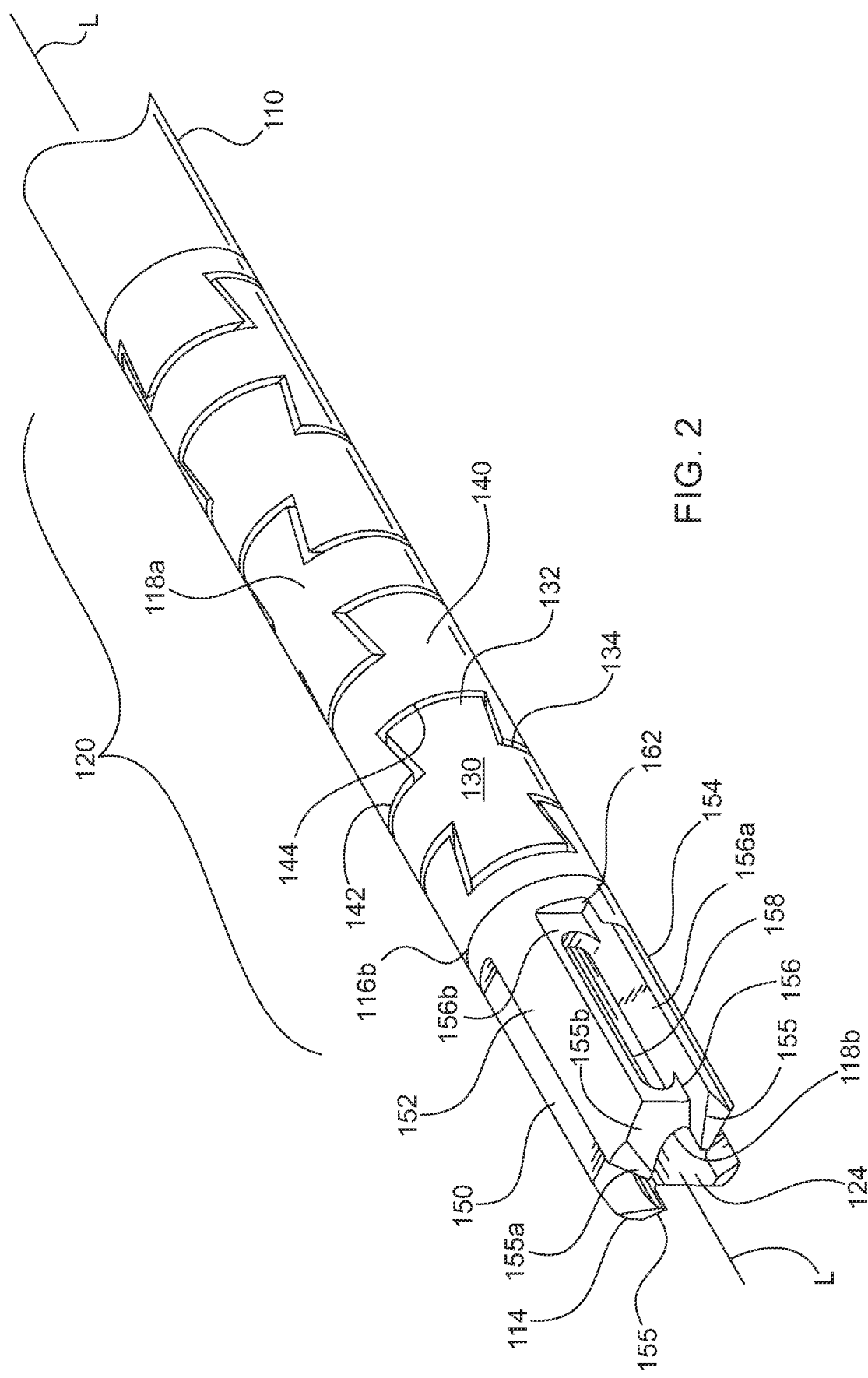
FIG. 2 is an enlarged perspective view of one section of the first device in accordance with an embodiment of the invention.

Referring now to FIGS. 1 and 2, a collection instrument 100 for collecting tissue from a body cavity will be described in accordance with one embodiment of the invention. Collection instrument 100 features a hollow tubular body in the form of a hollow shaft 110. Shaft 110 can be formed of any suitable medical grade material approved for surgical instrumentation, including but not limited to stainless steel. Shaft 110 includes a proximal end portion 111 that terminates at a proximal end 112 inside a handle portion 160. For illustration purposes, the section of proximal end portion 111 and proximal end 112 inside handle portion 160 are shown in dashed line. Shaft 110 also includes a distal end portion 113 that terminates at a distal end 114. Shaft 110 also includes a middle section 116 extending between proximal end portion 111 and distal end portion 113. Middle section 116 includes a first end 116a contiguous with and next to proximal end portion 111, and a second end 116b contiguous with and next to distal end portion 113. Shaft 110 features a tubular wall 118 extending between proximal end 112 and distal end 114. Tubular wall 118 defines an outer wall surface 118a and an inner wall surface 118b, the latter having a small area visible through the open distal end 114 in the Figures. In addition, tubular wall 118 defines and surrounds a passage 119 that is circular in cross section. Passage 119 extends from proximal end 112 of shaft 110 to distal end 114 of the shaft.

Middle section 116 of shaft 110 includes an articulating section 120 that allows distal end portion 113 and a portion of the middle section to articulate or bend relative to proximal end portion 111. Articulating sections in accordance with the invention can feature a variety of constructs that allow shaft 110 to articulate or bend. In one preferred embodiment, the articulating section includes a plurality of interlocking segments or elements, such as interlocking sections of the type and arrangement described in U.S. Pat. No. 8,366,559 entitled "Cannulated Flexible Drive Shaft", the content of which is incorporated by reference herein in its entirety and for all purposes. For example, the articulating section can incorporate a FlexMetric® brand flexible surgical shaft marketed by Lenkbar, LLC of Naples, Fla., USA.

Articulating section 120 includes a first interlocking section 130 and a second interlocking section 140. First interlocking section 130 has at least one pin 132 and at least one socket 134. Likewise, second interlocking section 140 has at least one pin 142 and at least one socket 144. Each pin is substantially triangular or trapezoidal shaped, and each socket is substantially triangular or trapezoidal shaped, having the same general shape as the corresponding pin. Pin 132 on first interlocking section 130 has a circumferential width that increases uniformly (i.e. at a constant rate) from outer wall surface 118a to inner wall surface 118b, so that the pin becomes gradually wider as it extends radially inwardly toward a longitudinal axis L of shaft 110. Pin 142 on second interlocking section 140 has a circumferential width that decreases uniformly (i.e. at a constant rate) from outer wall surface 118a to inner wall surface 118b, so that the pin becomes gradually narrower as it extends radially inwardly toward longitudinal axis L of shaft 110. The first and second interlocking sections 130 and 140 are cut at opposing angles to create at least one inward angled surface and at least one outward angled surface, the inward angled surface being adjacent to the outward angled surface.

Hollow shafts in accordance with the invention can be cannulated, with passages defined in various configurations. For example, passage 119 terminates at proximal end 112 to define a proximal opening 122 in shaft 110. Passage 119 also terminates at distal end 114 to define a distal opening 124 in shaft 110. Distal opening 124 is circular in cross section, as is the cross section of passage 119, as noted earlier. In this arrangement, distal opening 124 is designed to receive a solid or semi-solid core of bone marrow into passage 119 as shaft 110 is advanced through a bone cavity. Inner wall surface 118b forms a smooth, continuous and uninterrupted annular surface around passage 119 that slidingly receives a core. The smooth surface of inner wall surface 118b minimizes frictional forces and shear stresses so that the core is removed cleanly and in a preserved condition.

Distal end portion 113 also includes a core drill 150 that can shave bone and cut smoothly through bone marrow as shaft 110 is manually driven through a bone cavity. Core drill 150 has an outer wall 152 which coincides with and is coextensive with outer wall surface 118a of shaft. Thus, the outer diameter of core drill 150 is equal to the outer diameter of shaft 110. Core drill 150 is divided into four cutting sections 154, with each cutting section separated from adjacent cutting sections by recessed areas or flutes 156. Flutes 156 extend in a longitudinal direction parallel to longitudinal axis L. Each cutting section 154 terminates with a cutting edge 155 at distal end 114. In the example of FIG. 2, each flute 156 extends from the respective cutting edge 155 towards the second end 116b of the middle section 116 and terminates at a respective flute end 162. Each flute 156 is defined between a first flute face 156a and a second flute face 156b, with the first flute face 156a extending directly from the cutting edge 155, and the second flute face 156b being rotated around the longitudinal axis L relative to the first flute face 156a. Each flute face 166a, 156b extends parallel to the longitudinal axis L. The suction port 158 is separate from the distal opening 124 and located adjacent to the flute 156 and between the cutting edge 155 and the flute end 162. The illustrated suction port 158 extends through the second flute face 156b. Each cutting edge 155 is connected to the second flute face 156b of the adjacent flute 156 by a first connecting face 155a, and a second connecting face 155b, with the second connecting face 155b being angled greater than the first connecting face 155a relative to the longitudinal axis L.

As noted previously, shaft 110 is a versatile instrument that can remove bone marrow material by both coring and by aspiration. As such, shaft 110 functions in some instances as an auger-type tool that removes solid material in a preserved state from the body, and in other instances acts as a needle-type tool to remove liquid or fluid material by aspiration. With regard to aspiration, shafts in accordance with the invention can have one or more dedicated suction ports designed to aspirate fluid material from a bone cavity. For example, distal end portion 113 includes an elongated suction port 158 that extends through tubular wall 118 inside one of the flutes 156. Suction port 158 and distal opening 124 act as suction inlets to remove material during aspiration.

Distal end portion 113 is shown with only one suction port 158 through wall 118. Other embodiments in accordance with the invention can feature two, three or more suction ports through the tubular wall. The suction ports can all be located on the same cutting portion, or on more than one of the cutting portions. Therefore, it is contemplated that a shaft in accordance with the invention can feature a suction port on each cutting portion, with each suction port having an identical shape, relative position and relative orientation on its respective cutting portion as suction port 158. Suction port 158 has the shape of a long narrow slot. The narrow width (i.e. the short dimension shown in FIG. 2) of suction port 158, combined with the relatively long length to width ratio, promotes the entry of liquid material into shaft 110 during aspiration, while substantially preventing large fragments of solid material, such as coagulated material or bone fragments, from entering the shaft.

Tissue collection instruments in accordance with the invention can have a variety of handle configurations to be gripped by a physician. In preferred embodiments, a handle portion is provided at the proximal end of the tissue collection instrument. The preferred handle portion is ergonomically configured to permit the physician to comfortably grip the instrument and manually apply different types of force to the shaft via the handle. These forces can include pushing and pulling forces to advance and withdraw the shaft, respectively, as well as twisting forces to rotate the shaft. Certain combinations of pushing force and twisting force can also induce bending of shaft 110 at the articulation section 120 during advancement of the shaft through the bone cavity.

Collection instrument 100 includes a T-shaped handle portion 160 that is attached to proximal end 112 of shaft 110. Handle portion 160 includes a hex-shaped insert 170 and a winged portion 180 connected over the insert. Insert 170 has a proximal end 172 that provides a hub 174 for attaching other instruments to collection instrument 100. Insert 170 also includes a distal end 176 that connects handle portion 160 to shaft 110. Handle portions in accordance with the invention can be connected to shafts using any suitable connection, such as a pinned connection, a molded connection, or other alternative. In the present embodiment, distal end 176 of insert 170 is molded over proximal end 112 of shaft 110, and winged portion 180 is press fitted over insert 170. Winged portion 180 has two lateral extensions 181. When handle portion 160 is attached to shaft 110, lateral extensions 181 are arranged symmetrically with respect to longitudinal axis L.

Winged portion 180 includes a proximal end 182 and a distal end 184. Proximal end 182 defines a generally flat planar surface 183 on each lateral extension 181. In addition, distal end 184 defines a concave curvature or indent 185 on each lateral extension 181. The indents 185 are designed to allow the physician to wrap his or her fingers around winged portion 180, while resting his or her palm against planar surfaces 183 in a gripping position. In this gripping position, the physician can comfortably apply pushing force, pulling force, and twisting to shaft 110. The physician can also sense or detect conditions around shaft 110 by tactile feel when collection instrument 100 is navigated in a patient. For example, when distal end 114 of shaft 110 contacts an obstruction, the physician can immediately sense resistance to further advancement in the direction of the obstruction. This resistance force can be sensed, for example, when collection instrument 100 advances no further, or advances more slowly. The resistance force is felt by the physician as planar surface 183 bears against the physician's palm with increased force. The physician can also sense when shaft 110 bends or yields in response to contact with an obstruction by the change in resistance force felt through winged portion 180.

Collection devices in accordance with the invention can also include one or more features that assist the physician with visually monitoring the depth of insertion of the shaft inside the body. For example, shaft 110 includes a plurality of indicia 190 that are provided along outer wall surface 118a. Indicia 190 can be produced by any suitable process, including but not limited to laser cutting, laser marking, etching, or other means. Various types of indicia can be provided in accordance with the invention. For example, indicia 190 include a first indicia in the form of incrementally spaced hash marks or lines 192. Lines 192 extend circumferentially around outer wall surface 118a. Indicia 190 also include a second indicia in the form of numberings 194. Each numbering 194 is located adjacent to one of the lines 192 and corresponds to that line. The value of each numbering 194 represents a depth of insertion in centimeters. Each numbering 194 is an integer that represents the distance between its respective line 192 and distal end 114 of shaft 110. When shaft 110 is advanced into an incision, and a line 192 aligns with the patient's skin surface, the numbering 194 corresponding to that line at the skin surface indicates the depth to which distal end 114 is advanced into the body.

Shafts in accordance with the invention can feature articulating sections that span a small fraction of the shaft's overall length, or a large fraction of the shaft's overall length, so as to provide a desired degree of bending, i.e. a desired "pivot cone". For example, the longitudinal length of articulating section 120 is one-quarter or 25% of the total length of shaft 110. Therefore, 25% of the shaft length is comprised of interlocking segments that allow distal end 114 to bend and pivot with respect to proximal end 112. The remaining three-quarters or 75% of the total length of shaft 110 is a solid unitary section 117 that remains fixed in its orientation. Therefore, proximal end portion 111 and a majority of middle portion 116 are fixed in orientation, providing structural reinforcement that allows the shaft to be advanced through bone and tissue and maintain trajectory without buckling.

The length of the flexible section versus the length of the solid unitary section can of course be different in other embodiments. For example, a larger percentage of the length can be devoted to the articulating section to allow for a greater degree of bending and pivot motion. Alternatively, a smaller percentage of the length can be devoted to the articulating section to allow for a smaller degree of bending and pivot motion. As such, the length of the articulating section can be any percentage of the total length of the shaft, including but not limited to 5%, 10%, 15%, 20%, 25%, 30%, 35%, 40%, 45%, 50%, 55%, 60%, 65%, 70%, 75%, or 80% of the total length of the shaft. Percentages less than 5% or greater than 80% can also be used. Choosing a specific percentage allows the shaft's flexibility and pivot cone to be precisely controlled, unlike conventional flexible needles that are flexible along their entire lengths.

Figure 3:
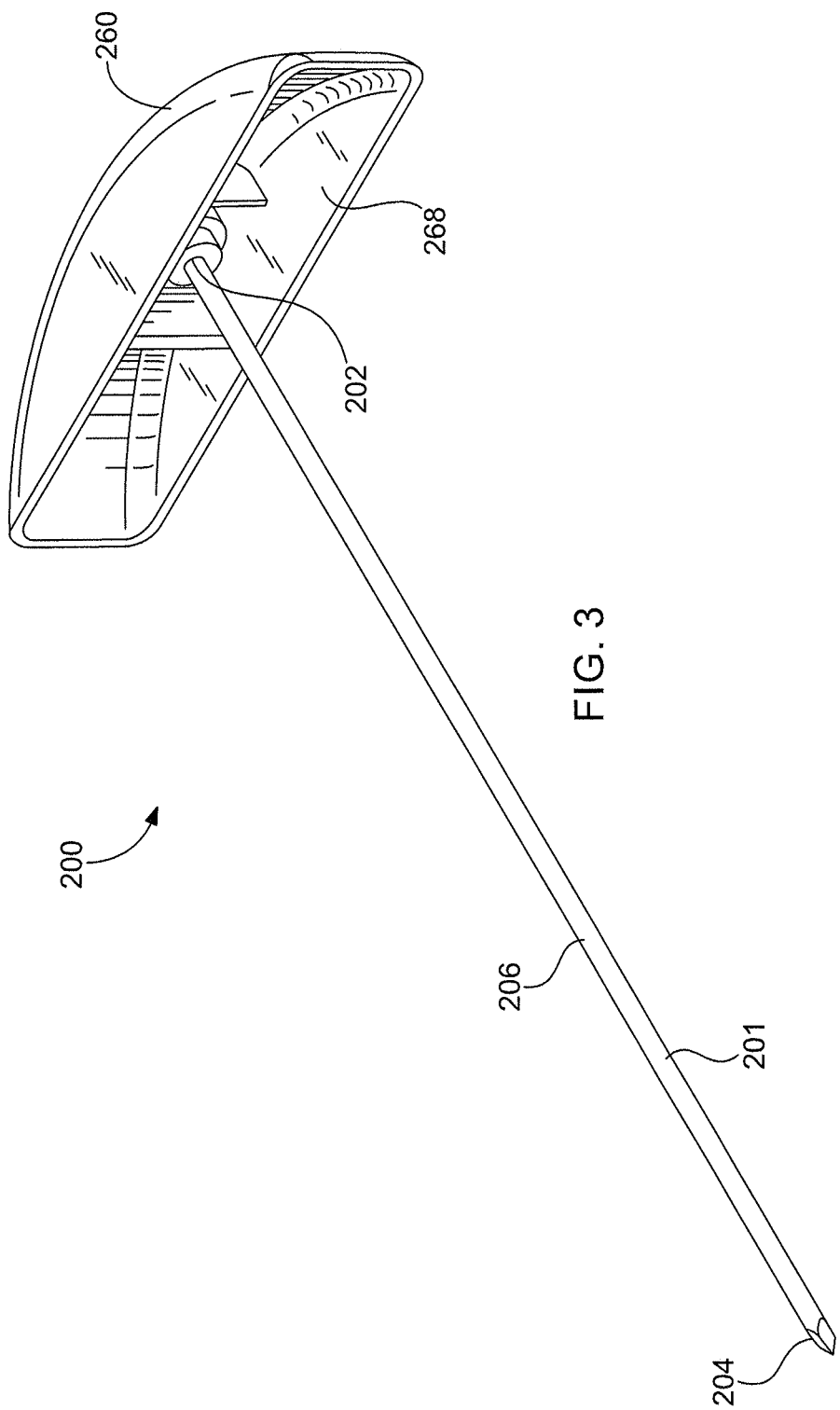
FIG. 3 is a perspective view of a second device for accessing a body cavity and collecting tissue from the body cavity in accordance with an embodiment of the invention, the second device being configured for use with the first device of FIG. 1.
Figure 4:
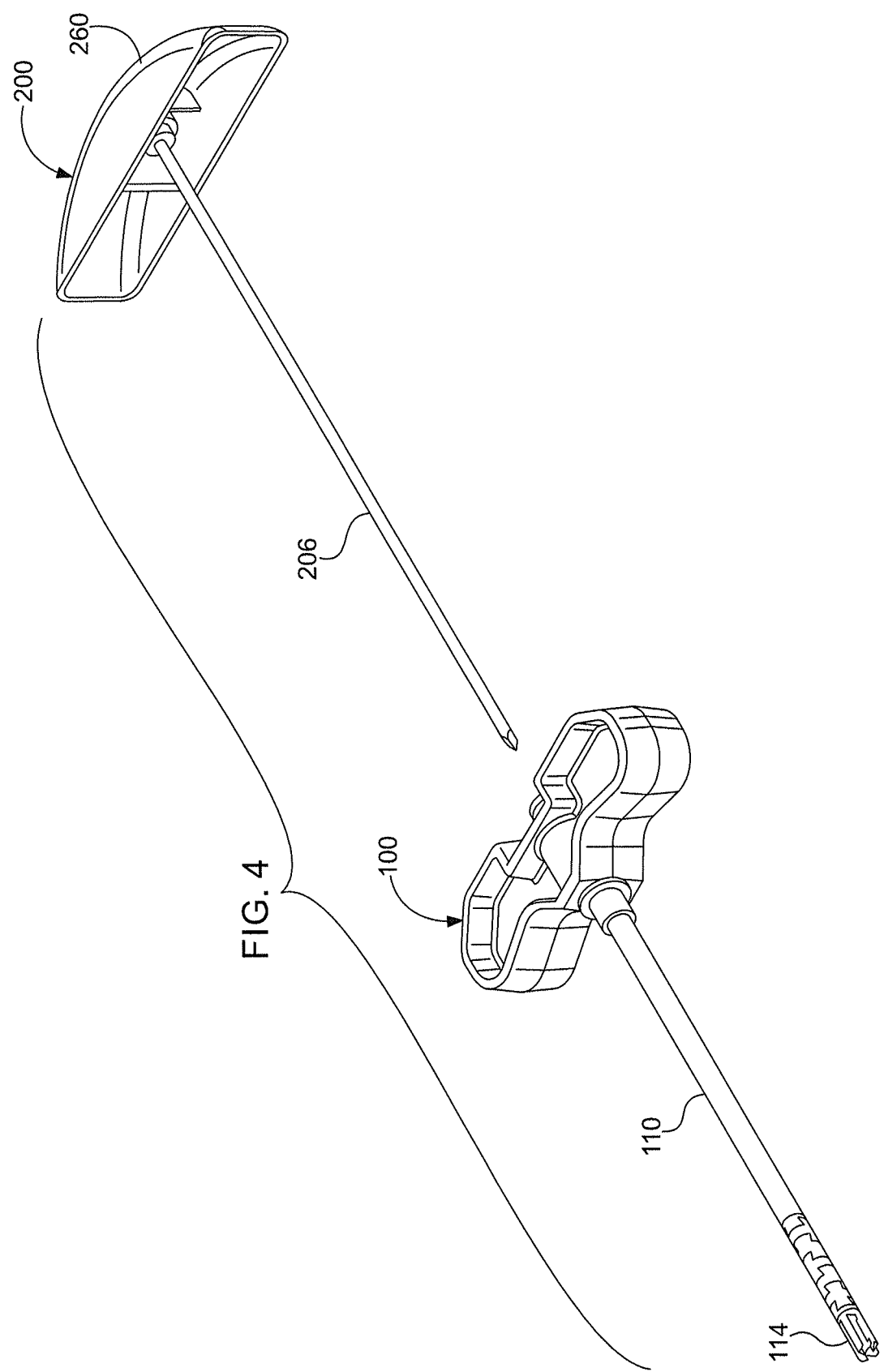
FIG. 4 is a perspective view of the first device of FIG. 1 and the second device of FIG. 3 in a disconnected state, the first and second devices arranged in an axially aligned position prior to being interconnected.
Figure 5:
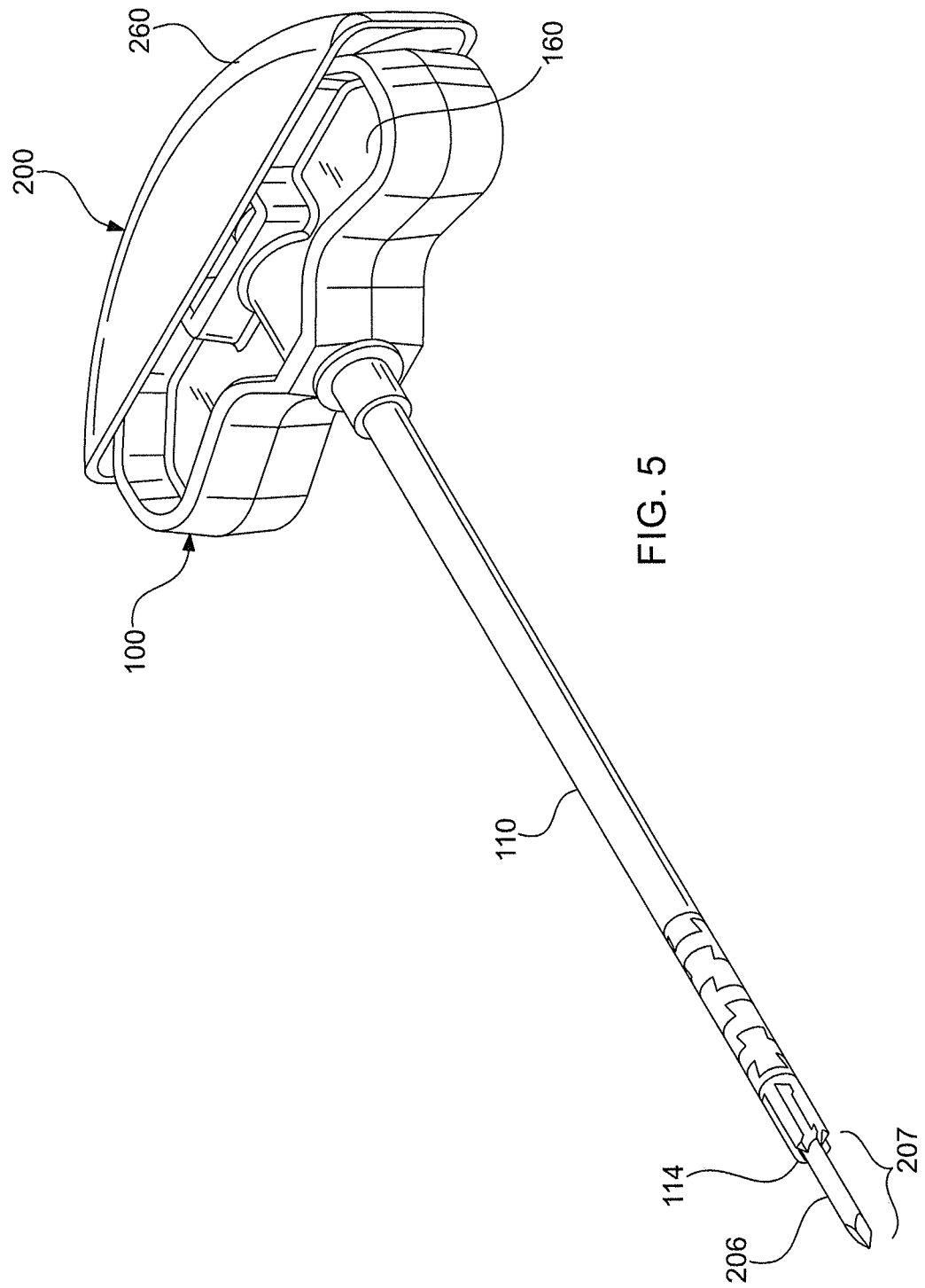
FIG. 5 is a perspective view of the first device of FIG. 1 and the second device of FIG. 3 assembled or coupled together in a connected state.
Figure 6:
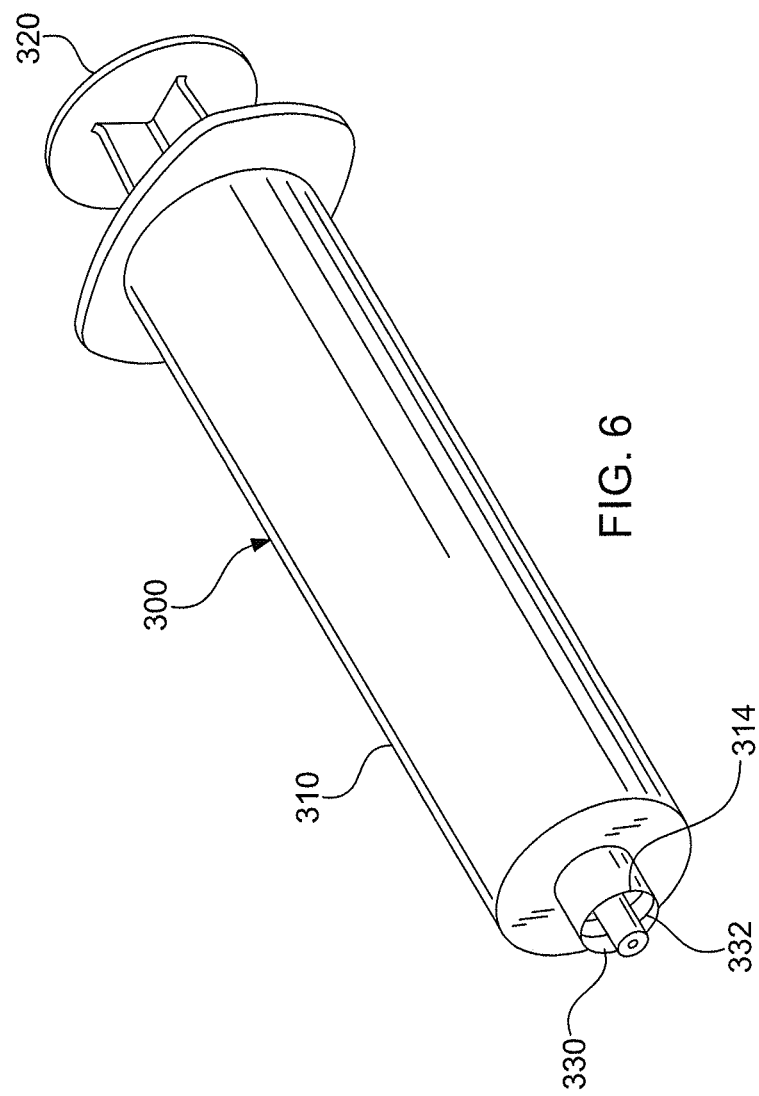
FIG. 6 is a perspective view of a third device in accordance with an embodiment of the invention that is configured for use with the first device of FIG. 1.
Figure 7:
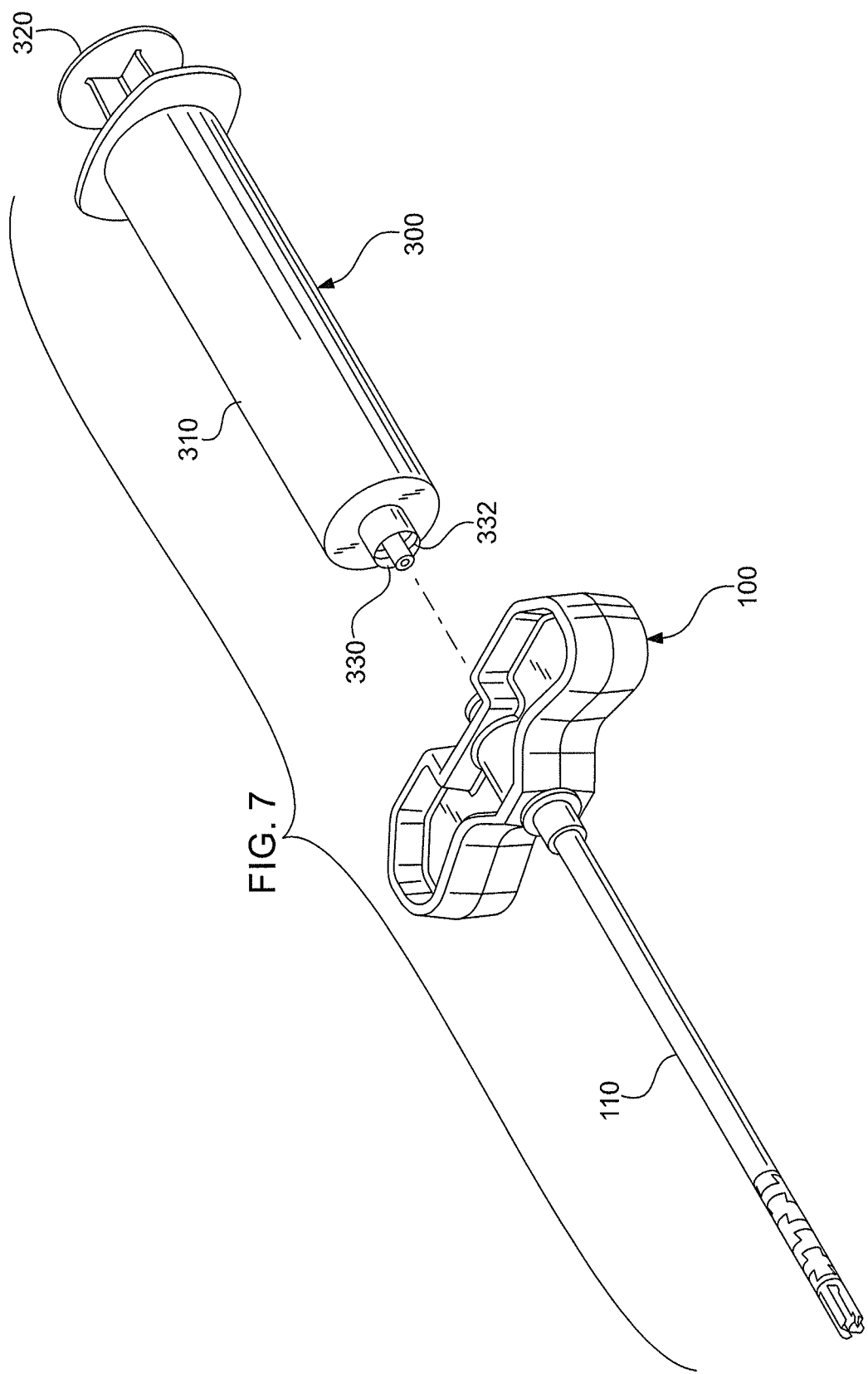
FIG. 7 is a perspective view of the first device of FIG. 1 and the third device of FIG. 6 in a disconnected state, the first and third devices arranged in an axially aligned position prior to being interconnected.
Figure 8:
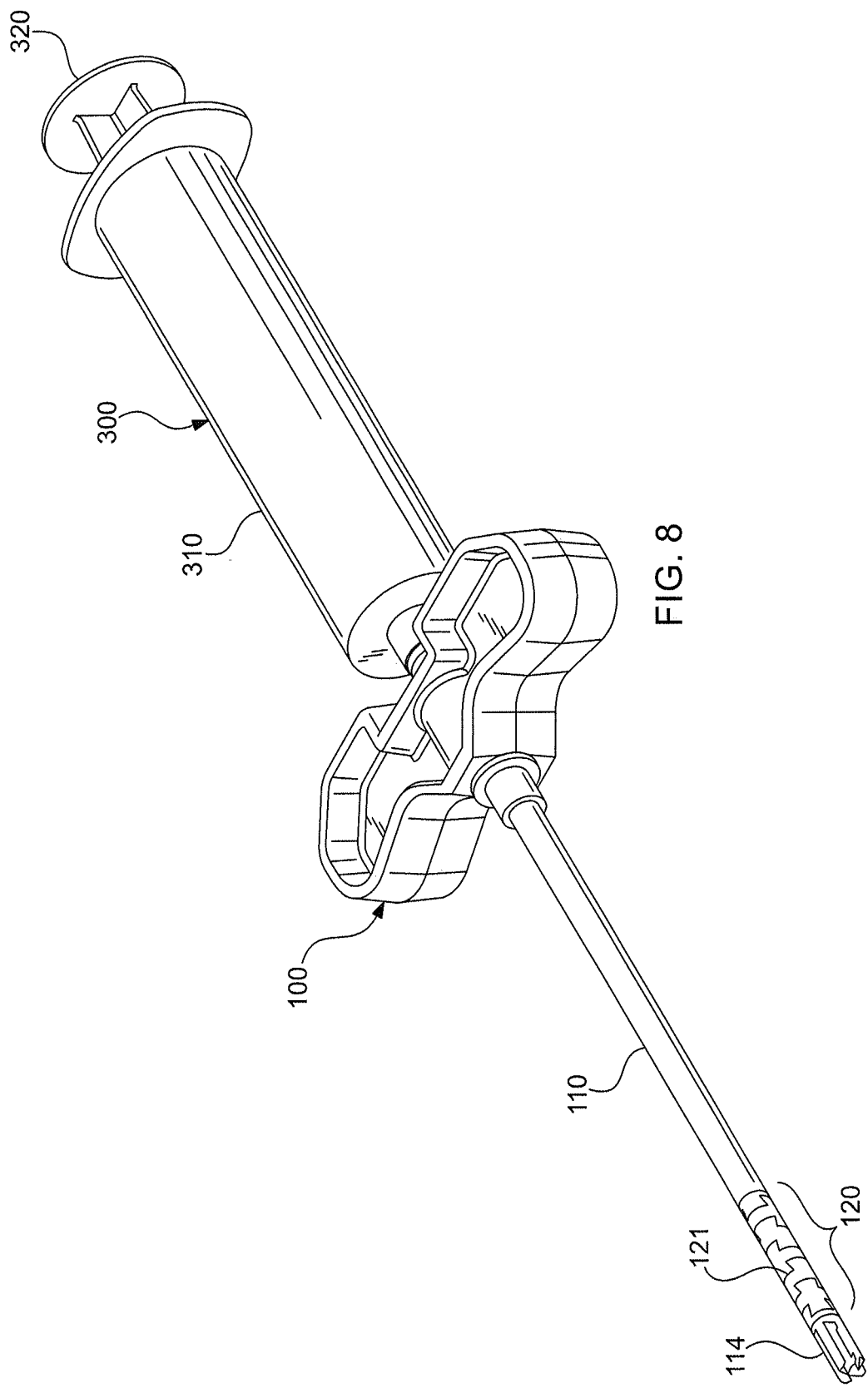
FIG. 8 is a perspective view of the first device of FIG. 1 and the third device of FIG. 6 assembled or coupled together in a connected state.

Collection instrument 100 can be used in combination with other instruments during different stages of a bone marrow harvesting procedure. Referring now to FIGS. 3-5, a piercing instrument 200 is shown in accordance with another embodiment of the invention. Piercing instruments in accordance with the invention can include tools for puncturing or piercing tissue and bone, including but not limited to trocars. For example, piercing instrument 200 includes a sharp-tipped trocar portion 201 with a proximal end 202, a distal end 204, and a shaft 206 extending between the proximal end and the distal end. Piercing instrument 200 also includes a generally T-shaped handle portion 260 attached to proximal end 202 of trocar portion 201.

The outer diameter of shaft 206 of trocar portion 201 is equal to or slightly smaller than the diameter of passage 119 in shaft 110. That is, the outer diameter of shaft 206 is equal to or slightly smaller than the inner diameter of shaft 110. In this configuration, passage 119 of shaft 110 is adapted to receive at least a portion of trocar portion 201 in a telescoping arrangement. In particular, shaft 206 of trocar portion 201 is adapted to be telescopically received into shaft 110, so that collection instrument 100 and piercing instrument 200 are interconnected as an assembly. The longitudinal dimension or length of shaft 206 is slightly longer than the longitudinal dimension or length of shaft 110. As such, a small leading portion 207 of shaft 206 projects beyond distal end 114 of shaft 110 in an exposed manner when trocar portion 201 is fully inserted into collection instrument 100, as shown in FIG. 5.

When trocar portions in accordance with the invention are fully inserted into tissue collection instruments, the handles of the two instruments preferably lock, nest or otherwise engage one another to limit movement of either instrument relative to the other instrument. For example, handle portion 260 is generally hollow and defines a recess 268 that conforms to the outer geometry of handle portion 160. In this configuration, recess 268 receives winged portion 180 of handle portion 160 in a snug fit when trocar portion 201 is fully inserted into shaft 110 of collection instrument 100, as shown in FIG. 5. The snug fit secures the two handle portions 160, 260 and their respective shafts together in a fixed assembly that only allows piercing instrument 200 to be withdrawn from collection instrument 100, while preventing further advancement of the piercing instrument through shaft 110, and preventing rotation of the piercing instrument relative to the collection instrument.

Collection instruments in accordance with the invention can also be connected to sources of negative pressure for purposes of aspirating material in liquid form. Referring now to FIGS. 6-10, collection instrument 100 is shown with a source of negative pressure in the form of a suction syringe 300. Suction syringe 300 includes a generally cylindrical collection chamber 310 and a plunger 320 that is axially displaceable inside the chamber to either draw fluid into the chamber under negative pressure, or to eject fluid from the chamber under positive pressure. Collection chamber 310 has a distal end 314 that attaches to hub 174 on collection instrument 100. Syringes and collection devices in accordance with the invention can be attached to one another using any suitable attachment means. For example, distal end 314 of collection chamber 310 attaches to hub 174 in a fluid tight connection using a threaded Luer connection 330. Luer connection 330 has a female threaded surface 332 that mates with a male threaded surface 175 on hub 174.

When suction syringe 300 is attached to collection instrument 100, plunger 320 can be pulled in a proximal direction to create negative pressure or suction inside shaft 110. Liquid material that is present outside distal end portion 113 is drawn into shaft 110 in response to negative pressure created in passage 119. Preferably, the forces that draw liquid into the passage are concentrated at the one or more suction ports 158, but may also be present at distal opening 124. The suction port(s) 158 and distal opening 124 are not the only openings in shaft 110 that can draw in liquids however. The interlocking sections of articulating section 120 are separated from one another by cutting lines that leave small gaps 121 through tubular wall 118. Such gaps 121 could potentially draw in liquids. It is preferred that liquids only be drawn through the one or more suction ports and the distal opening. Therefore, preferred assemblies in accordance with the invention include one or more mechanisms to seal gaps 121 when negative pressure is applied inside shaft 110.

Figure 9:
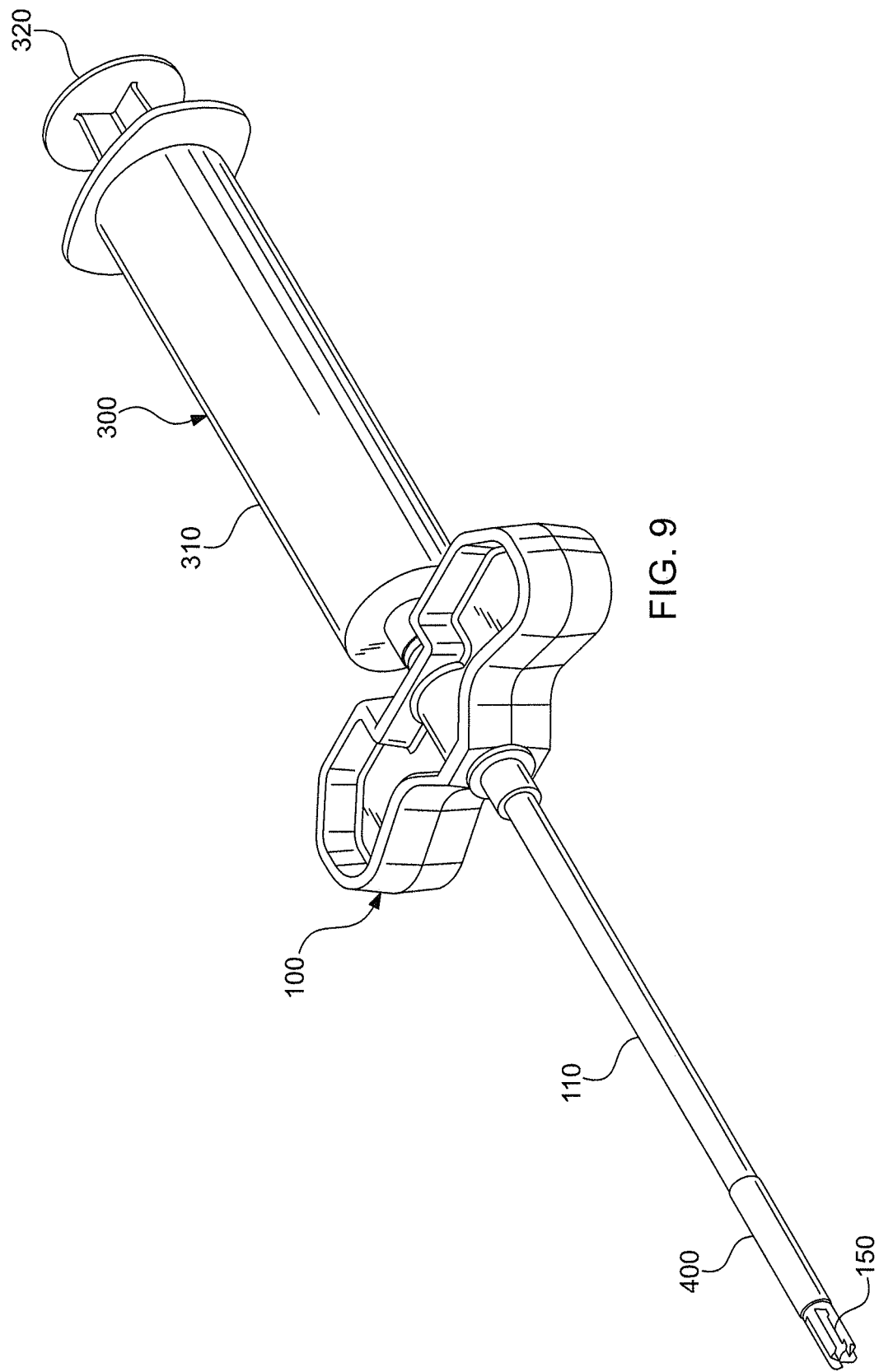
FIG. 9 is a perspective view of the first device of FIG. 1 and the third device of FIG. 6 assembled or coupled together in a connected state, shown with a first optional accessory on the first device.

Referring to FIG. 9, instrument 100 is shown with an external mechanism in accordance with one embodiment for sealing gaps 121 between interlocking sections of articulating section 120. The external mechanism is in the form of a flexible sheath or sleeve 400 placed over shaft 110 in a position covering gaps 121. In this position, sleeve 400 prevents suction forces from drawing in liquid through the gaps. This, in turn, allows more negative pressure to develop inside shaft 110 to draw in more fluids through suction port(s) 158. Sleeve 400 can be formed of any suitable medical material, including but not limited to medical grade plastic or silicone.

Figure 10:
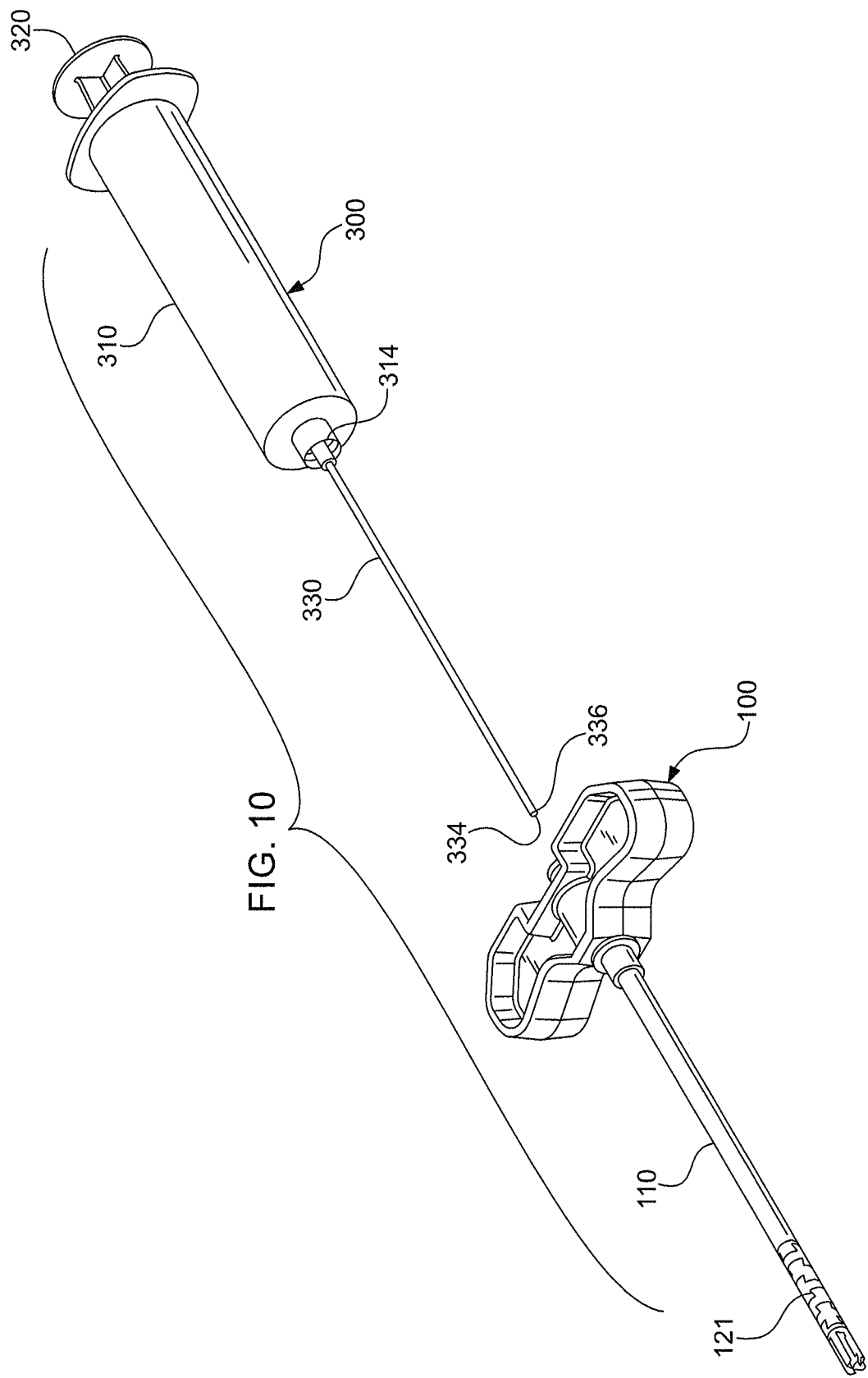
FIG. 10 is a perspective view of the first device of FIG. 1 and the third device of FIG. 6 in a disconnected state, shown with a second optional accessory attached to the third device.

Referring to FIG. 10, instrument 100 is shown with an internal mechanism in accordance with another embodiment for sealing gaps 121 between interlocking sections of articulating section 120. The internal mechanism is in the form of a flexible cannula or suction tube 330 that attaches to syringe 300 generally, and more specifically, to the distal end 314 of collection chamber 310. When plunger 320 is pulled to draw material into suction syringe 300, negative pressure is created inside flexible cannula 330 and draws material into a distal end opening 334 defined at the distal end 336 of the cannula. The length of flexible cannula 330 can be such that the distal end 336 of the cannula terminates at a location adjacent to the suction port(s) 158 and distal to gaps 121 when suction syringe 330 is attached to collection device 100. The sidewall 331 of flexible cannula 330 preferably engages inner wall surface 118a of shaft 110 inside articulating section 120 to effectively seal off gaps 121 and prevent liquid from being drawn through the gaps.

Example—Bone Marrow Harvesting Procedure

Figure 11:
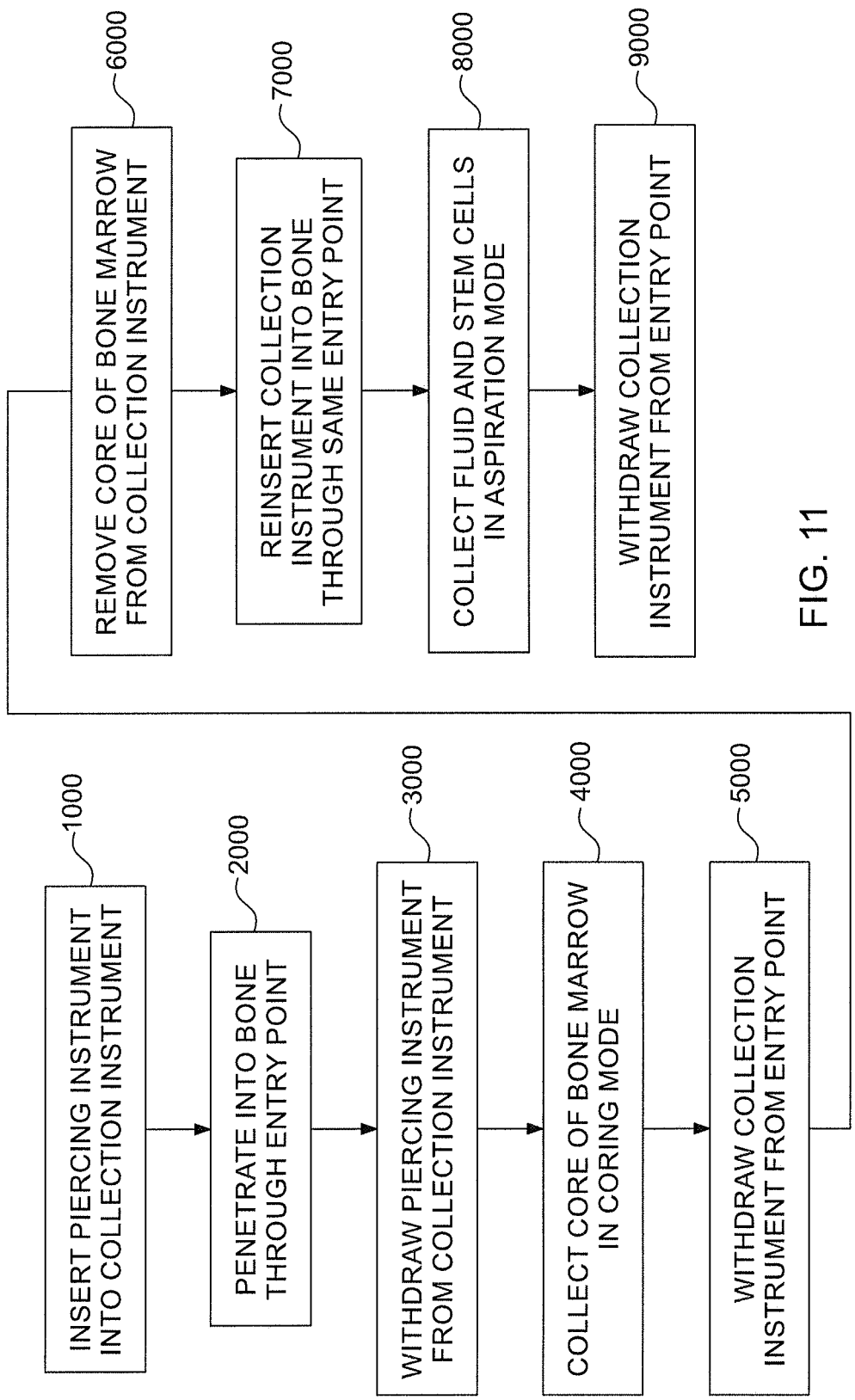
FIG. 11 is a block diagram of a tissue collection procedure in accordance with another embodiment of the invention.

Referring to FIG. 11, one possible tissue collection procedure in accordance with the invention is shown in block diagram form. In this example, the procedure is a bone marrow harvesting procedure in which bone marrow and stems cells are collected from a patient's anterior or posterior ilium. The previously described collection instrument 100, piercing instrument 200, and suction syringe 300 will be referenced when describing individual steps. Other devices can also be used to carry out the method in accordance with the invention. In addition, the steps can be performed with or without additional steps known to physicians and medical professionals of ordinary skill in the art.

In step 1000, the piercing instrument 200 is inserted through handle portion 160 of collection instrument 100 and into passage 119 of shaft 110 until the distal end of the piercing instrument is exposed through the distal end of the shaft. Prior to this step, the physician may apply an anticoagulant to surfaces on tissue collection instrument 100 and piercing instrument 200 to prevent matter from clotting, particularly on the inside of the collection instrument.

A small incision is made in the patient's skin over the hip area, and the patient's tissue is bluntly dissected to expose the surface of the ilium. Tissue collection instrument 100 and piercing instrument 200 are then inserted into the incision and advanced to the exposed bone surface, at which time the sharp tip or point is placed on the desired entry point through the bone. The physician then presses their palm firmly against the winged portion 180 of handle portion 160 to apply axial pressure on the bone, while rotating the handle portion in a clockwise direction. Tissue collection instrument 100 and piercing instrument 200 are rotated in unison while axial pressure is maintained to manually drive piercing instrument 200 and shaft 110 through the cortical bone. The simultaneous application of axial pressure and rotation are continued until tissue collection instrument 100 and piercing instrument 200 completely penetrate through the cortical bone and enter the cavity in step 2000. The moment of entry into the cavity can be sensed through tactile feel, as the amount of resistance to axial advancement drops the moment that the cortical bone is fully penetrated and no longer provides resistance. Entry into the bone cavity can also be confirmed using imaging. Once tissue collection instrument 100 and piercing instrument 200 enter the bone cavity, the piercing instrument is withdrawn from the tissue collection instrument in step 3000, leaving the tissue collection instrument in place in the bone.

At this stage, tissue collection instrument 100 is used in a coring mode to collect a core of bone marrow in step 4000. Handle portion 160 is simultaneously twisted and advanced to collect the bone marrow. Shaft 110 is no longer supported internally by piercing instrument 200, and now has a moderate amount of freedom to bend. Nevertheless, the degree of flexibility of articulating section 120 is limited, so that shaft 110 is able to advance through bone marrow, albeit not in a straight path. The limited flexibility of articulating section 120 causes distal end portion 113 to yield under resistance as it advances through marrow and/or contacts the inner aspect of the bone. This results in a bending movement that alters the direction of advancement as the collection instrument 100 is advanced, which prevents inadvertent penetration beyond the marrow space adding a safety advantage to the process Tissue collection device 100 is simultaneously advanced and rotated through the bone like an auger until a core of bone marrow in the path of movement is collected inside passage 119 of shaft 110. Shaft 110 is advanced into the ilium to a desired depth corresponding to the desired amount of marrow to be removed. For example, shaft 110 can be inserted to a depth of 3-4 cm. Once shaft 110 reaches the desired depth, further advancement is halted and the tissue collection device 100 is withdrawn from the patient in step 5000. The core of bone marrow inside shaft 110 is then carefully removed from the shaft in step 6000. The bone marrow can be removed from the shaft using a suitable instrument, such as piercing instrument 200 or other implement that can dislodge the core of bone marrow from passage 119.

The removal of bone marrow from the bone can leave a void space in the bone cavity. Bone marrow in and around the void space can be agitated during insertion and/or removal of collection instrument from the bone cavity. This agitation can leave a fluid dispersion of stem cells and blood cells in the void space. At this stage, collection instrument 100 is operated in an aspiration mode to collect the stem cells dispersed in and around the void space. Collection instrument 100 is reinserted back through the same incision and entry point of the bone, and into the void space in step 7000. In some instances, the physician may elect to insert piercing instrument 200 back into collection instrument 100 before reinserting the collection instrument into the incision. Piercing instrument 200 can provide an aid for finding the entry hole in the bone and inserting shaft 110 through the hole. Shaft 110 is advanced into the void space until distal end 114 of the shaft is located at an optimal position for drawing in stem cells.

To operate collection instrument 100 in the aspiration mode, the physician connects suction syringe 300 to collection instrument 100 by attaching distal end 314 of the suction syringe to hub 174 of the collection instrument. Negative pressure is then applied to the shaft to collect fluid and stem cells in the aspiration mode in step 8000. To introduce negative pressure in the shaft, plunger 320 is pulled back, i.e. in a proximal direction away from collection instrument 100. As negative pressure builds in shaft 110, fluid and stem cells in the void space enter the shaft through the one or more suction ports 158 and travel up into collection chamber 310 of suction syringe 300. The volume of fluid that is drawn into suction syringe can vary depending on various factors, including but not limited to the volume of the void space created during the prior coring step. The physician may elect to withdraw approximately 20 cubic centimeters of fluid, for example, to collect the fluid dispersion of stem cells. Once the desired volume of fluid is collected in collection chamber 310, syringe 300 can be disconnected from collection instrument 100, and the collected fluid with stem cells can be used immediately in a point-of-care application or transferred to storage for subsequent usage and/or processing. At this stage, the physician can withdraw the collection instrument 100 from the entry point and remove the instrument from the patient in step 9000. Alternatively, the physician can reinsert collection instrument 100 back through the same incision and same entry point of the bone to collect additional material. For example, collection instrument 100 can remain connected with syringe 300 and guided into the same void space for further aspiration, or to a different location for aspiration. In such cases, steps 7000 and 8000 can be repeated. Alternatively, shaft 110 can be advanced into a new area in the bone to collect another core of bone marrow. In such a case, steps 4000-6000 can be repeated.

Although the invention is illustrated and described herein with reference to specific embodiments, the invention is not intended to be limited to the details shown. Rather, various modifications, combinations, substitutions and/or rearrangements can be made with respect to the components and their features shown herein, with any such modification, combination, substitution and/or rearrangement being contemplated within the scope and range of equivalents of the claims and without departing from the invention.

What is claimed:

1. An instrument for collecting tissue from a body cavity, the collection instrument comprising a hollow tubular body, the tubular body comprising a proximal end portion that terminates at a proximal end, a distal end portion that terminates at a distal end, and a middle section extending between the proximal end portion and the distal end portion, the middle section having a first end contiguous with and next to the proximal end portion, and a second end contiguous with and next to the distal end portion, the tubular body comprising a tubular wall extending between the proximal end and the distal end, the tubular wall defining an outer wall surface and an inner wall surface, the tubular wall surrounding a passage that extends from the proximal end portion of the tubular body to the distal end portion of the tubular body, the tubular body comprising an articulating section that allows a portion of the tubular body to articulate relative to the proximal end portion, the distal end portion comprising at least one suction port extending from the outer wall surface to the inner wall surface, the at least one suction port providing a path of fluid communication between the outer wall surface and the passage for drawing in said tissue from a body cavity when the tubular body is connected to a source of negative pressure, and when the distal end portion is placed in proximity to said tissue from a body cavity, the passage terminating at the distal end to define a distal opening, the distal end portion of the tubular body defining a core drill for smoothly shaving bone and collecting a core of bone marrow in a preserved state as the tubular body is advanced into a bone cavity, the core drill comprising at least a first cutting section and a second cutting section, with the passage extending between the first and second cutting sections and adapted to receive said core of bone marrow in said preserved state through said distal opening, the core drill having an outer wall adjacent to the outer wall surface of the tubular body, the outer wall of the core drill being cylindrical and having a uniform diameter along its entire length, and wherein:

the first cutting section comprises a first cutting edge at the second distal end and a first flute extending parallel to the longitudinal axis of the tubular body from the first cutting edge towards the second end of the of the middle section and terminating at a first flute end, the second cutting section comprises a second cutting edge at the second distal end and a second flute extending parallel to the longitudinal axis of the tubular body from the second cutting edge towards the second end of the of the middle section and terminating a second flute end, and the at least one suction port is separate from the distal opening and located adjacent to the first flute and between the first cutting edge and the first flute end.

2. The collection instrument of claim 1, wherein the passage terminates at the proximal end to define a proximal opening in the tubular body.

3. An assembly for collecting tissue from a body cavity, the assembly comprising:

a piercing instrument comprising a first proximal end, a first distal end, and a shaft extending between the first proximal end and the first distal end; and a collection instrument comprising a hollow tubular body, the tubular body comprising a proximal end portion that terminates at a second proximal end, a distal end portion that terminates at a second distal end, and a middle section extending between the proximal end portion and the distal end portion, the middle section having a first end contiguous with and next to the proximal end portion, and a second end contiguous with and next to the distal end portion, the tubular body comprising a tubular wall extending between the second proximal end and the second distal end, the tubular wall defining an outer wall surface and an inner wall surface, the tubular wall surrounding a passage that extends from the proximal end portion of the tubular body to the distal end portion of the tubular body, the passage adapted to receive at least one portion of the piercing instrument in a telescoping arrangement, the middle section of the tubular body comprising an articulating section that allows a portion of the tubular body to articulate relative to the proximal end portion, the distal end portion comprising at least one suction port extending from the outer wall surface to the inner wall surface, the at least one suction port providing a path of fluid communication between the outer wall surface and the passage for drawing in said tissue from a body cavity when the tubular body is connected to a source of negative pressure, and when the distal end portion is placed in proximity to said tissue from a body cavity, the passage terminating at the second distal end to define a distal opening, the distal end portion of the tubular body defining a core drill for smoothly shaving bone and collecting a core of bone marrow in a preserved state as the tubular body is advanced into a bone cavity, the core drill comprising at least a first cutting section and a second cutting section, with the passage extending between the first and second cutting sections and adapted to receive said core of bone marrow in said preserved state through said distal opening, the core drill having an outer wall adjacent to the outer wall surface of the tubular body, the outer wall of the core drill being cylindrical and having a uniform outer diameter size along its entire length, and wherein:

the first cutting section comprises a first cutting edge at the second distal end and a first flute extending parallel to the longitudinal axis of the tubular body from the first cutting edge towards the second end of the of the middle section and terminating at a first flute end, the second cutting section comprises a second cutting edge at the second distal end and a second flute extending parallel to the longitudinal axis of the tubular body from the second cutting edge towards the second end of the of the middle section and terminating a second flute end, and the at least one suction port comprises at least one first suction port that is separate from the distal opening and located adjacent to the first flute and between the first cutting edge and the first flute end.

4. The assembly of claim 3, wherein the piercing instrument comprises a first handle, and the collection instrument comprises a second handle that is nestable with the first handle when the at least one portion of the piercing instrument is received in the passage of the collection instrument.

5. An assembly for collecting tissue from a body cavity, the assembly comprising:

a source of negative pressure comprising a suction element; and a collection instrument comprising a hub portion and a hollow tubular body, the hub portion comprising a connecting element for connection to the suction element, the tubular body comprising a proximal end portion, a distal end portion, and a middle section extending between the proximal end portion and the distal end portion, the proximal end portion terminating at a proximal end, and the distal end portion terminating at a distal end, the middle section having a first end contiguous with and next to the proximal end portion, and a second end contiguous with and next to the distal end portion, the tubular body comprising a tubular wall extending between the proximal end and the distal end, the tubular wall defining an outer wall surface and an inner wall surface, the tubular wall surrounding a passage that extends from the proximal end portion of the tubular body to the distal end portion of the tubular body, the middle section of the tubular body comprising an articulating section that allows a portion of the tubular body to articulate relative to the proximal end portion, and the distal end portion comprising at least one suction port extending from the outer wall surface to the inner wall surface, the at least one suction port providing a path of fluid communication between the outer wall surface and the passage, the connecting element adapted to form a fluid connection between the suction element and the passage for drawing said tissue from a body cavity through the suction port and into the passage upon activation of the source of negative pressure when the suction element is connected to the hub portion, and when the distal end portion is placed in proximity to said tissue from a body cavity, the passage terminating at the distal end to define a distal opening, the distal end portion of the tubular body defining a core drill for smoothly shaving bone and collecting a core of bone marrow in a preserved state as the tubular body is advanced into a bone cavity, the core drill comprising at least a first cutting section and a second cutting section, with the passage extending between the first and second cutting sections and adapted to receive said core of bone marrow in said preserved state through said distal opening, the core drill having an outer wall adjacent to the outer wall surface of the tubular body, the outer wall of the core drill being cylindrical and having a uniform outer diameter size along its entire length, and wherein:

the first cutting section comprises a first cutting edge at the second distal end and a first flute extending parallel to the longitudinal axis of the tubular body from the first cutting edge towards the second end of the of the middle section and terminating at a first flute end, the second cutting section comprises a second cutting edge at the second distal end and a second flute extending parallel to the longitudinal axis of the tubular body from the second cutting edge towards the second end of the of the middle section and terminating a second flute end, and the at least one suction port comprises at least one first suction port that is separate from the distal opening and located adjacent to the first flute and between the first cutting edge and the first flute end.

6. The assembly of claim 5, wherein the source of negative pressure comprises a syringe.

7. The assembly of claim 5, wherein the articulating section comprises a first interlocking section and a second interlocking section.

8. The assembly of claim 5, wherein the collection instrument comprises an outer sleeve positioned over the articulating section to seal the articulating section.

9. The assembly of claim 5, wherein the source of negative pressure comprises a suction tube that extends into the passage, the suction tube comprising a tube distal end that terminates adjacent to the suction port of the tubular body when the suction element is connected to the hub portion.

10. The assembly of claim 3, wherein the passage is cylindrical between the first cutting section and the second cutting section.

11. The assembly of claim 3, wherein the passage defines a smooth continuous inner wall surface to slidingly receive said core of bone marrow in said preserved state.

12. The assembly of claim 5, wherein the passage is cylindrical between the first cutting section and the second cutting section.

13. The assembly of claim 5, wherein the passage defines a smooth continuous inner wall surface to slidingly receive said core of bone marrow in said preserved state.

14. The assembly of claim 3, wherein the at least one first suction port comprises a plurality of first suction ports.

15. The assembly of claim 3, wherein the at least one suction port further comprises at least one second suction port that is separate from the distal opening and located adjacent to the second flute and between the second cutting edge and the second flute end.

16. The assembly of claim 3, wherein the at least one suction port comprises a slot that is elongated along the longitudinal axis.

17. The assembly of claim 3, wherein each flute is defined between a respective first flute face and a respective second flute face, with the first flute face extending along parallel to the longitudinal axis from the cutting edge, and the second flute face being rotated around the longitudinal axis L relative to the first flute face.

18. The assembly of claim 17, wherein at least one suction port extends through the second flute face.

19. The assembly of claim 17, wherein the first cutting edge is connected to the respective second flute face of the second cutting section by a first connecting face, and a second connecting face, with the second connecting face being angled greater than the first connecting face relative to the longitudinal axis L.

20. The assembly of claim 5, wherein the at least one first suction port comprises a plurality of first suction ports.

21. The assembly of claim 5, wherein the at least one suction port further comprises at least one second suction port that is separate from the distal opening and located adjacent to the second flute and between the second cutting edge and the second flute end.

22. The assembly of claim 5, wherein the at least one suction port comprises a slot that is elongated along the longitudinal axis.

23. The assembly of claim 5, wherein each flute is defined between a respective first flute face and a respective second flute face, with the first flute face extending along parallel to the longitudinal axis from the cutting edge, and the second flute face being rotated around the longitudinal axis L relative to the first flute face.

24. The assembly of claim 23, wherein at least one suction port extends through the second flute face.

25. The assembly of claim 23, wherein the first cutting edge is connected to the respective second flute face of the second cutting section by a first connecting face, and a second connecting face, with the second connecting face being angled greater than the first connecting face relative to the longitudinal axis L.

* * * * *